US00PP16585P2

(12) United States Plant Patent
Bradford

(10) Patent No.: US PP16,585 P2
(45) Date of Patent: May 30, 2006

(54) NECTARINE TREE NAMED 'SUGARINE I'

(50) Latin Name: *Prunus persica*
Varietal Denomination: Sugarine I

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 149 days.

(21) Appl. No.: 11/029,688

(22) Filed: Jan. 6, 2005

(51) Int. Cl.
*A01H 5/00* (2006.01)

(52) U.S. Cl. ..... Plt./190
(58) Field of Classification Search ..... Plt./190
See application file for complete search history.

(56) References Cited

U.S. PATENT DOCUMENTS

PP5,228 P * 5/1984 Zaiger ..... Plt./190
PP7,507 P 4/1991 Bradford
PP9,359 P 11/1995 Bradford
PP11,968 P2 * 7/2001 Bradford ..... Plt./190

* cited by examiner

*Primary Examiner*—Anne Marie Grunberg
*Assistant Examiner*—W. C. Haas

(57) ABSTRACT

The present invention relates to a nectarine tree, *Prunus persica*, and more particularly to a new and distinct variety broadly characterized by a medium size, vigorous, hardy, self-fertile, productive and regular bearing tree. The fruit matures under the ecological conditions described in late June, with the first picking Jun. 25, 2004. The fruit is uniformly large in size, sub-acidic and very sweet in flavor, globose in shape, clingstone in type, firm in texture, yellow in flesh color, and mostly red in skin color. The variety was developed as a first generation cross using 'Bright Pearl' (U.S. Plant Pat. No. 9,359) white flesh nectarine as the selected seed parent and 'Spring Bright' (U.S. Plant Pat. No. 7,507) yellow flesh nectarine as the selected pollen parent.

1 Drawing Sheet

Latin name: *Prunus persica.*
Varietal denomination: 'Sugarine I'.

BACKGROUND OF THE VARIETY

In a continuing effort to improve the quality of shipping fruits, I, the inventor, typically hybridize a large number of peach, nectarine, plum, apricot, and cherry seedlings each year. The present invention relates to a new and distinct variety of nectarine tree, which has been denominated varietally as 'Sugarine I'. The present variety was hybridized by me in 1996, grown as a seedling on its own root in my greenhouse, and transplanted to a cultivated area of my experimental orchard at Bradford Farms near Le Grand, Calif. in Merced County (San Joaquin Valley). The variety was developed as a first generation cross using 'Bright Pearl' (U.S. Plant Pat. No. 9,359) white flesh nectarine as the selected seed parent and 'Spring Bright' (U.S. Plant Pat. No. 7,507) yellow flesh nectarine as the selected pollen parent. A single tree from the stated cross was selected as the claimed variety. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its selected seed parent, 'Bright Pearl' (U.S. Plant Pat. No. 9,359) nectarine, by producing nectarines that are nearly globose in shape, mostly red in skin color, firm in texture, clingstone in type, and very sweet and sub-acid in flavor, but is quite distinguished thereform by producing nectarines that are yellow instead of white in flesh color and that mature about two weeks earlier.

The present variety is most similar to its selected pollen parent, 'Spring Bright' (U.S. Plant Pat. No. 7,507) nectarine, by producing nectarines that are nearly globose in shape, very firm in texture, clingstone in type, yellow in flesh color, and nearly full red in skin color, but is distinguished therefrom by producing fruit that matures about two weeks later, that is larger in size, and that is sweeter and sub-acidic instead of acidic in flavor.

SUMMARY OF VARIETY

In summary, the present variety is characterized by a medium size, vigorous, hardy, self-fertile, productive and regular bearing tree. The fruit matures under the ecological conditions described in late June, with the first picking Jun. 25, 2004. The fruit is uniformly large in size, sub-acidic and very sweet in flavor, globose in shape, clingstone in type, firm in texture, yellow in flesh color, and mostly red in skin color.

DRAWING

The accompanying photograph exhibits four whole fruits positioned to display the characteristics of the skin color and form, one fruit divided transversely to the suture plane to reveal the flesh and stone, and typical leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Jun. 28, 2004, on the original tree during its eighth growing season. It is to be noted that the 2004 stone fruit season was abnormally early in maturing times for all varieties, thus skewing the starting calendar dates approximately two weeks forward. All major color code designations are by reference to the Inter-Society Color Council, National Bureau of Standards. Common color names are also used occasionally.

TREE

Size: Medium, reaching a height of 10' [3.05 m.] and a spread of 10' [3.05 m.] after eight growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Trained by pruning to be vase formed.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning necessary.

Fertility: Self-fertile.

Bearing: Regular bearer with no alternate bearing yet observed.

Trunk:

*Size.*—Medium, with a maxium diameter of 4¼" [108 mm.] after the eighth growing season.

*Texture.*—Shaggy.

*Bark color.*—Grayish brown [61. gy.Br] with Deep brown [56. deep Br.] variegation.

*Lenticels.*—Approximate Number Per Square Inch: 8. Color: Dark orange yellow [72. d. OY]. Typical Size: 3/16" [4.8 mm.] to 7/16" [11.1 mm.]. Shape: Eye-shaped to elongated.

Branches:

*Size.*—Diameter of main scaffold is 2½" [64 mm.] measured 12" above the crotch, diameter of limb is 1¾" [44 mm.] measured 12" above the first fork, typical of *Prunus persica*, and dependent upon cultural practices and climatic conditions.

*Texture.*—Smooth on first year wood, increasing roughness with age.

*Color.*—1st Year Wood Topside: Grayish red [19. gy.R]. 1st Year Wood Underside: Brilliant yellow green [116. brill.YG]. Older Wood: Deep yellowish brown [75. deep yBr].

*Lenticels.*—Approximate Number per Square Inch: 45. Color: Dark orange yellow [72. d.OY]. Size: 1/16" [1.6 mm.] to 3/16" [4.8 mm.]. Shape: Eye-shaped to elongated.

Leaves:

*Size.*—Medium. Average Length: 5⅜" [137 mm.]. Average Width: 1½" [38 mm.].

*Arrangement.*—Alternate.

*Thickness.*—Medium.

*Form.*—Elliptical.

*Apex.*—Acuminate.

*Base.*—Acute with an average base angle of 80 degrees.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Vein color.*—Light yellow green [119. l.YG].

*Petiole.*—Average Length: ⅜" [9.5 mm]. Average Thickness: 1/16" [1.6 mm.]. Color: Brilliant yellow green [116. brill.YG].

*Stipules.*—Number: 2 to 6 per growing tip. Average Length: ¼" [6.4 mm.]. Color: Brilliant yellow green [116. brill.YG] becoming Dark grayish reddish brown [47. d.gy.rBr] with age.

*Glands.*—Number: 2 to 4. Position: Mostly alternate. Size: Small. Form: Globose. Color: Light yellow green [119. l.YG] when young becoming Light olive brown [94. l.OlBr] with age.

*Leaf buds.*—Pointed, medium in size.

Flower buds:

*Hardiness.*—Hardy, with respect to central California winters.

*Diameter.*—Typically 5/16" [7.9 mm.] 1 week before bloom.

*Length.*—Typically ½" [12.7 mm.] 1 week before bloom.

*Form.*—Not appressed.

*Surface.*—Pubescent.

*Color.*—Deep purplish pink [248. deep pPk].

Flowers: Perfect, complete, perigynous, usually a single pistil, typically thirty or more stamens, five sepals and petal locations alternately positioned.

*Type.*—Showy, large.

*Average flower diameter.*—1¾" [44.5 mm.].

*Number of petals.*—Usually five, with a small percentage of double blossoms observed.

*Petal shape.*—Circular.

*Petal margin.*—Somewhat wavy.

*Average petal diameter.*—¾" [19.1 mm.].

*Average petal length.*—13/16" [20.6 mm.].

*Petal apex.*—Rounded.

*Petal base.*—Rounded to slightly truncate.

*Petal color.*—Moderate purplish pink [250. m.pPk].

*Anther color.*—Deep red [13. deep R] surrounding a Light orange yellow [70. l.OY] center.

*Stigma color.*—Light greenish yellow [101. l.gY].

*Sepal color.*—Very deep purplish red [257. v.deep pR].

*Sepal length.*—9/32" [7.1 mm.].

*Sepal width.*—¼" [6.4 mm.].

*Average pistil length.*—⅝" [15.9 mm.].

*Average stamen length.*—9/16" [14.3 mm.].

*Fragrance.*—Moderate.

*Blooming period.*—Medium to late compared with other varieties.

*Onset of bloom.*—One percent on Mar. 4, 2004.

*Date of full bloom.*—Mar. 14, 2004.

*Duration of bloom.*—One to two weeks, dependant on ambient temperature.

*Number per cluster.*—1 to 3 with single flowers most common.

FRUIT

Maturity when described: Hard ripe, Jun. 28, 2004.

Date of first picking: Jun. 25, 2004, but typically July $9^{th}$ on a normal year.

Date of last picking: Jul. 7, 2004, but typically July 21st on a normal year.
Size: Uniform.
*Average diameter axially.*—3" [76.2 mm.].
*Average diameter across suture plant.*—2⅞" [73.0 mm.].
*Average diameter across the cheek plane.*—2⅞" [73.0 mm.].
*Typical weight.*—8.7 ounces [247 grams].
Form: Globose, symmetrical.
*Longitudinal section form.*—Oval to slightly obovate.
*Transverse section through diameter.*—Circular.
Suture: A shallow groove from the base that extends beyond the pistil point, sharper and deeper at the stem cavity and apex.
Ventral surface: Rounded, lipped stronger toward the apex on both sides.
Lips: Equal.
Cavity: Flaring, elongated in the suture plane, suture showing on one side, Light orange yellow [70. l.OY] stem markings typical.
*Depth.*—⅝" [15.9 mm.].
*Breadth.*—1⅛" [28.6 mm.].
Base: Rounded to slightly truncate.
Apex: Rounded, but cordate if viewed parallel to the suture.
Pistil point: Mostly apical, negligible in length, depressed within the suture.
Stem: Medium.
*Average length.*—⅜" [9.5 mm.].
*Average Width.*—3/16" [4.8 mm.].
Skin:
*Thickness.*—Medium.
*Surface.*—Smooth.
*Tenacity.*—Tenacious to flesh.
*Astringency.*—Nonastringent.
*Tendency to crack.*—None observed.
*Color.*—Primarily Very deep red [14. v.deep R] smoothly blending into a Moderate red [15. m.R] background with only slight Brillant orange yellow [67. brill.OY] freckling toward the apex.
Flesh:
*Color.*—Brilliant yellow [83. brill.Y] with very slight Strong red [12. s.R] flecking very near the stone.
*Surface of pit cavity.*—Strong pink [2. s.Pk] fibers breaking when twisted from the stone.
*Amygdalin.*—Scarce.
*Juice.*—Abundant, rich.
*Texture.*—Very firm, crisp.
*Fibers.*—Abundant, fine.
*Ripens.*—Slightly earlier at the apex.
*Flavor.*—Very sweet and sub-acid, typically 16 brix.
*Aroma.*—Very slight.
*Eating quality.*—Excellent.

STONE

Type: Clingstone.
Form: Oval.
Hilum: Narrow, oblong.
Base: Slightly oblique.
Apex: Acute, with an average tip angle of 45 degrees and a length of ⅛" [3.2 mm.].
Sides: Equal.
Surface: Irregularly furrowed and ridged towards the apex, pitted toward the base.
Ridges: Jagged toward the base.
External color: Strong yellowish brown [74. s.yBr].
Pit wall color when cracked: Moderate yellowish brown [77. m.yBr].
Cavity surface color: Deep yellowish brown [75. deep yBr].
Average pit wall thickness: ¼" [6.4 mm.]
Average width: 1¼" [31.8 mm.].
Average length: 1½" [38.1 mm.].
Average breadth: ⅞" [22.2 mm.].
Tendency to split: Minimal.
Kernel:
*Form.*—Oval.
*Skin color.*—Pale yellow [89. p.Y] when freshly cracked.
*Pellicle color.*—Light grayish yellowish brown [79. l.gy.yBr].
*Taste.*—Sweet.
*Viable.*—Yes.
*Average width.*—½" [12.7 mm.].
*Average length.*—13/16" [20.6 mm.].
*Amygdalin.*—Scant.

USE

Market: Fresh market and long distance shipping.
Keeping quality: Good. Fruit quality observed to remain in good condition after 17 days in standard cold room at 36° Fahrenheit [2° Celsius].
Shipping quality: Good.
Resistance to insects: No unusal susceptibilities noted.
Resistance to diseases: No unusual susceptibilities noted.

Other Notes

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to its selected pollen parent, 'Spring Bright' (U.S. Plant Pat. No. 7,507) nectarine, by producing nectarines that are nearly globose in shape, very firm in texture, clingstone in type, yellow in flesh color, and nearly full red in skin color, but is distinguished therefrom by producing fruit that matures about two weeks later, that is larger in size, and that is sweeter and sub-acidic instead of acidic in flavor.

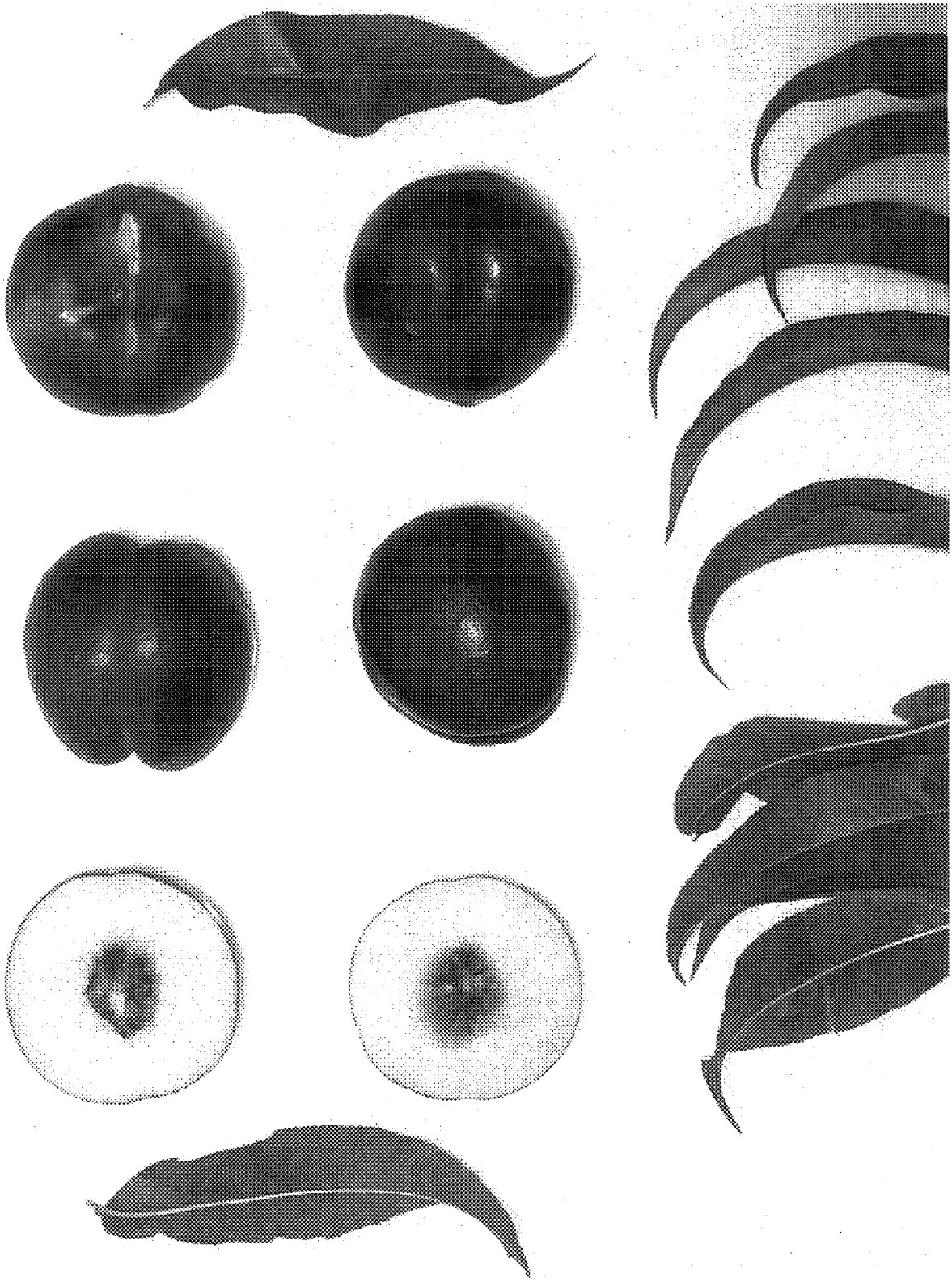

* * * * *